United States Patent
Murakami (10) Patent No.: US 9,671,348 B2
(45) Date of Patent: Jun. 6, 2017

(54) METHOD FOR MEASURING COMPONENT BY TREATING AQUEOUS SAMPLE WITH ALPHA-KETO ACID AND THEN CONVERTING COMPONENT TO HYDROGEN PEROXIDE

(75) Inventor: Tomomi Murakami, Shizuoka (JP)

(73) Assignee: KYOWA MEDEX CO., LTD., Chuo-ku, Tokyo (JP)

( * ) Notice: Subject to any disclaimer, the term of this patent is extended or adjusted under 35 U.S.C. 154(b) by 0 days.

(21) Appl. No.: 13/991,652

(22) PCT Filed: Dec. 12, 2011

(86) PCT No.: PCT/JP2011/078669
§ 371 (c)(1),
(2), (4) Date: Jun. 5, 2013

(87) PCT Pub. No.: WO2012/081539
PCT Pub. Date: Jun. 21, 2012

(65) Prior Publication Data
US 2013/0288283 A1    Oct. 31, 2013

(30) Foreign Application Priority Data

Dec. 13, 2010   (JP) ................ 2010-276550

(51) Int. Cl.
*C12Q 1/54*   (2006.01)
*G01N 21/77*   (2006.01)
(Continued)

(52) U.S. Cl.
CPC ............ *G01N 21/77* (2013.01); *C09B 21/00* (2013.01); *C12Q 1/28* (2013.01); *G01N 21/78* (2013.01); *G01N 2333/908* (2013.01)

(58) Field of Classification Search
None
See application file for complete search history.

(56) References Cited

U.S. PATENT DOCUMENTS 4,614,714 A * 9/1986 Kusakabe et al. ............... 435/25
5,037,738 A * 8/1991 Lamos .................. C12Q 1/54
435/12
(Continued)

FOREIGN PATENT DOCUMENTS

CN  101097200  1/2008
CN  101173939  5/2008
(Continued)

OTHER PUBLICATIONS

Aoyama, "H2O2-POD group", Clinical Testing, vol. 41, No. 9 (1997) 1014-19.
(Continued)

*Primary Examiner* — Erin M Bowers
(74) *Attorney, Agent, or Firm* — Fitzpatrick Cella Harper and Scinto (57) ABSTRACT

The present invention provides a method for measuring a component to be measured in a sample, comprising converting the component to be measured in the sample into hydrogen peroxide and measuring the formed hydrogen peroxide in the presence of an α-keto acid using an oxidative-coloring chromogen. The present invention also provides a method for suppressing the influence of a peroxide on a method of converting a component to be measured in a sample into hydrogen peroxide and measuring the formed hydrogen peroxide using an oxidative-coloring chromogen, the suppression method comprising using an α-keto acid. The measuring method and the suppression method of the present invention using an α-keto acid suppress the influence of a peroxide to give an accurate measurement of the component to be measured in the sample.

7 Claims, 3 Drawing Sheets

(51) Int. Cl.
*C12Q 1/28* (2006.01)
*G01N 21/78* (2006.01)
*C09B 21/00* (2006.01)

(56) References Cited

U.S. PATENT DOCUMENTS

| | | | |
|---|---|---|---|
| 2008/0241816 A1* | 10/2008 | Taniguchi | G01N 21/78 435/4 |
| 2008/0295259 A1 | 12/2008 | Ueda et al. | |
| 2009/0023167 A1 | 1/2009 | Miyauchi et al. | |

FOREIGN PATENT DOCUMENTS

| | | |
|---|---|---|
| CN | 101609017 | 12/2009 |
| EP | 2 065 708 | 6/2009 |
| EP | 2 093 288 | 8/2009 |
| JP | 57-147058 | 9/1982 |
| JP | 59-182361 | 10/1984 |
| JP | 60-178356 | 9/1985 |
| JP | 60-178358 | 9/1985 |
| JP | 61-284661 | 12/1986 |
| JP | 03-049695 | 3/1991 |
| JP | 04-194664 | 7/1992 |
| JP | 07-039394 | 10/1995 |
| JP | 9-511746 | 11/1997 |
| JP | 11-318440 | 11/1999 |
| JP | 2002-356421 | 12/2002 |
| JP | 2003-231632 | 8/2003 |
| JP | 2004-089191 | 3/2004 |
| JP | 2004-217932 | 8/2004 |
| JP | 2007-204701 | 8/2007 |
| JP | 2008-125368 | 6/2008 |
| JP | 2008-125368 A * | 6/2008 |
| JP | 2008-201968 | 9/2008 |
| JP | 2009-125049 | 6/2009 |
| WO | 95/27501 | 10/1995 |
| WO | 2006/085654 | 8/2006 |

OTHER PUBLICATIONS

Fossati, et al., "Use of 3,5-Dichloro-2-hydroxybenzenesulfonic Acid/4-Aminophenazone Chromogenic System in Direct Enzymic Assay of Uric Acid in Serum and Urine", Clin. Chem., vol. 26, No. 2 (1980) 227-31.

Marzocchi, et al., "Chemiluminiscent detection systems of horseradish peroxidase employing nucleophilic acylation catalyst", Analytic Biochemistry, vol. 377, No. 2 (2008) 189-94.

Yang, et al., "Oxidation of Phenothiazines by Human Term Placental Peroxidase in Non-Smokers", Teratogenesis, Carcinogensis, and Mutagenesis, vol. 18 (1997) 139-51.

* cited by examiner

METHOD FOR MEASURING COMPONENT BY TREATING AQUEOUS SAMPLE WITH ALPHA-KETO ACID AND THEN CONVERTING COMPONENT TO HYDROGEN PEROXIDE

This application is a National Phase of PCT Application No. PCT/JP2011/078669 filed Dec. 12, 2011, which in turn claims benefit of Japanese Application No. 2010-276550 filed Dec. 13, 2010.

TECHNICAL FIELD

The present invention relates to a method for measuring a component to be measured in a sample, a reagent for measurement, a kit for measurement, and a method for suppressing the influence of a peroxide.

BACKGROUND ART

In clinical diagnosis, which employs a biological sample such as whole blood, serum, plasma, or urine, the measurement of a component to be measured in the biological sample is practiced. The component to be measured in the biological sample is measured by, for example, an enzymatic method or immunoassay using antigens and antibodies. The enzymatic assay of the component to be measured in the biological sample often involves converting the component to be measured into hydrogen peroxide by the action of oxidase, then reacting the formed hydrogen peroxide, in the presence of a peroxidase, with an oxidative-coloring chromogen, and measuring the absorbance of the resulting dye.

This measurement of the component to be measured in the biological sample based on the hydrogen peroxide quantification system is frequently used in continuous multi-sample measurement using an automatic analyzer, because of its mild reaction conditions, convenient operation, etc. This method, however, is susceptible to bilirubin, hemoglobin, or the like, present in the biological sample to disadvantageously receive a so-called negative influence, giving a measurement value lower than a theoretical value. To solve this problem, methods have previously been reported, such as a method using an iron-cyano compound (e.g., non-patent document 1).

Meanwhile, a surfactant is often used in the measurement of the component to be measured in the biological sample based on the hydrogen peroxide quantification system. The surfactant is used for a control of an enzyme specificity based on an interaction with a substrate of the enzyme, a control of an enzyme reactivity based on an interaction with the enzyme, the pretreatment of the sample, etc. Above all, polyoxyalkylene surfactants such as a polyoxyethylene surfactant or a polyoxypropylene surfactant is frequently used because of diversity of their types and availability.

Polyoxyalkylene surfactants, however, tend to form peroxides due to their structure (e.g., patent document 1). The peroxides formed have a disadvantageous positive influence on the hydrogen peroxide quantification system, thus giving a measurement value higher than a theoretical value. In particular, in cases where the conditions of storing a reagent or a kit for measuring biological samples are insufficient, peroxides are often formed in the reagent or kit, thereby causing deterioration in their performance.

In many cases, diagnosis kits comprise additives such as a salt, a buffer, an enzyme, and an antiseptic. Such kits may contain peroxides which are formed therein or come to be mixed from outside during the course of their production. In addition, peroxides may be formed by oxidation in such kits in the course of their prolonged storage. These peroxides may have a positive influence upon measurement using the kits. In addition, biological samples, such as whole blood, serum, plasma, or urine, may contain peroxides formed due to in vivo oxidative stress, enzyme reactions, administration of drugs, or the like. The peroxides so formed may have a positive influence upon measurement.

Pyruvic acid, one of α-keto acids, is formed as an intermediate product in the in vivo glycolytic system. The pyruvic acid is known to have relatively strong antioxidative activity (e.g., patent document 2). Also, its effect of neutralizing oxygen radicals in cells has been reported (e.g., patent document 3).

There is a demand for a measuring method whereby the influence of a peroxide is suppressed in the measurement of the component to be measured in the biological sample based on the hydrogen peroxide quantification system.

PRIOR ART DOCUMENTS

Patent Documents

Patent Document 1: Japanese unexamined Patent Application Publication No. 2007-204701
Patent Document 2: Japanese unexamined Patent Application Publication No. 2004-217932
Patent Document 3: Japanese unexamined Patent Application Publication (Translation of PCT Application) No. 09-511746

Non-Patent Document

Non-patent Document 1: Clinical Chemistry, Vol. 26, No. 2, p. 227-231 (1980)

SUMMARY OF THE INVENTION

Problems to be Solved by the Invention

An object of the present invention is to provide a method for measuring a component to be measured in a sample, a reagent therefor, and a kit therefor, whereby the influence of a peroxide on the hydrogen peroxide quantification system is suppressed, and to provide a method for suppressing the influence of a peroxide.

Means to Solve the Problems

The present inventors have conducted diligent studies to solve the problems and consequently found that use of an α-keto acid in a method of converting a component to be measured in a sample into hydrogen peroxide and measuring the formed hydrogen peroxide can suppress the influence of a peroxide without influencing the hydrogen peroxide quantification system, whereby the component to be measured in the sample can be measured accurately. On the basis of the findings, the present invention has been completed. Specifically, the present invention relates to the following [1] to [20]:

[1] A method for measuring a component to be measured in a sample, comprising converting the component to be measured in the sample into hydrogen peroxide and measuring the formed hydrogen peroxide in the presence of an α-keto acid using an oxidative-coloring chromogen.

[2] A method for suppressing the influence of a peroxide on a method for measuring a component to be measured in a sample comprising converting the component to be measured in the sample into hydrogen peroxide and reacting the formed hydrogen peroxide with an oxidative-coloring chromogen, wherein the suppression method comprises reacting the formed hydrogen peroxide with the oxidative-coloring chromogen in the presence of an α-keto acid.

[3] The method according to [1] or [2], wherein the α-keto acid is an α-keto acid selected from the group consisting of pyruvic acid, α-ketoglutaric acid, and oxaloacetic acid.

[4] The method according to any one of [1] to [3], wherein the oxidative-coloring chromogen is a leuco chromogen.

[5] The method according to [4], wherein the leuco chromogen is a phenothiazine derivative.

[6] The method according to [5], wherein the phenothiazine derivative is 10-(carboxymethylaminocarbonyl)-3,7-bis(dimethylamino)phenothiazine.

[7] The method according to any one of [1] to [3], wherein the oxidative-coloring chromogen is an oxidative coupling-type chromogen.

[8] The method according to [7], wherein the oxidation coupling-type chromogen is a combination of a coupler and an aniline derivative or a phenol derivative.

[9] A reagent for measurement of a component to be measured in a sample, comprising a hydrogen peroxide-forming reagent, an α-keto acid, a peroxidative substance, and an oxidative-coloring chromogen.

[10] The reagent according to [9], wherein the α-keto acid is an α-keto acid selected from the group consisting of pyruvic acid, α-ketoglutaric acid, and oxaloacetic acid.

[11] The reagent according to [9] or [10], wherein the oxidative-coloring chromogen is a leuco chromogen.

[12] The reagent according to [11], wherein the leuco chromogen is a phenothiazine derivative.

[13] The reagent according to [12], wherein the phenothiazine derivative is 10-(carboxymethylaminocarbonyl)-3,7-bis(dimethylamino)phenothiazine.

[14] The reagent according to [9] or [10], wherein the oxidative-coloring chromogen is an oxidative coupling-type chromogen.

[15] The reagent according to [14], wherein the oxidative coupling-type chromogen is a combination of a coupler and an aniline derivative or a phenol derivative.

[16] A kit for measurement of a component to be measured in a sample, comprising a first reagent and a second reagent, wherein the first reagent comprises one of a leuco chromogen and a peroxidative substance and the second reagent comprises the other of a leuco chromogen and a peroxidative substance separately, and a hydrogen peroxide-forming reagent and an α-keto acid are independently comprised in one or both of the first reagent and the second reagent.

[17] The kit according to [16], wherein the leuco chromogen is a phenothiazine derivative.

[18] The kit according to [17], wherein the phenothiazine derivative is 10-(carboxymethylaminocarbonyl)-3,7-bis(dimethylamino)phenothiazine.

[19] A kit for measurement of a component to be measured in a sample, comprising a first reagent and a second reagent, wherein the first reagent comprises one of (i) a coupler and (ii) an aniline derivative or a phenol derivative and the second reagent comprises the other of (i) a coupler and (ii) an aniline derivative or a phenol derivative separately, and a peroxidative substance, a hydrogen peroxide-forming reagent and an α-keto acid are comprised in one or both of the first and second reagent independently.

[20] The kit according to any one of [16] to [19], wherein the α-keto acid is an α-keto acid selected from the group consisting of pyruvic acid, α-ketoglutaric acid, and oxaloacetic acid.

Effect of the Invention

The present invention provides a method, a reagent and a kit for measuring a component to be measured in a sample, whereby the influence of a peroxide is suppressed, and also provides a method for suppressing the influence of a peroxide.

MODE OF CARRYING OUT THE INVENTION (1) Method for Measuring a Component to be Measured The method for measuring an analyte according to the present invention comprises converting the component to be measured in the sample into hydrogen peroxide and measuring the formed hydrogen peroxide in the presence of an α-keto acid using an oxidative-coloring chromogen. The method for measuring a component to be measured according to the present invention can suppress the influence of a peroxide present in the sample and accurately measure the component in the sample.

The sample according to the present invention is not particularly limited as long as the measuring method of the present invention can be performed. Examples thereof include whole blood, serum, plasma, and urine.

The measuring method of the present invention is not particularly limited as long as the method enables the suppression of the influence of a peroxide. Examples thereof include a method comprising the following steps:

Step 1: the step of reacting the component to be measured in the sample with a hydrogen peroxide-forming reagent to form hydrogen peroxide;

Step 2: the step of reacting the hydrogen peroxide formed in step 1, in the presence of an α-keto acid and a peroxidative substance, with an oxidative-coloring chromogen, to form a dye;

Step 3: the step of measuring the absorbance of the dye formed in step 2;

Step 4: the step of correlating the absorbance measured in step 3 with a calibration curve representing the relationship between concentration of the component and absorbance or between activity of the component and absorbance, the calibration curve being prepared using the components having known concentrations; and Step 5: the step of determining the concentration or the activity of the component in the sample.

The reaction of step 1 can be performed in the presence of an α-keto acid. Also, step 1 and step 2 can be performed simultaneously or in stages.

The reaction of the component to be measured in the sample with a hydrogen peroxide-forming reagent in step 1 can be performed under any reaction condition as long as hydrogen peroxide is formed. For example, the reaction is performed at 10 to 50° C., preferably 20 to 40° C., for 1 minute to 3 hours, preferably 2.5 minutes to 1 hour.

The reaction of the hydrogen peroxide with an oxidative-coloring chromogen in the presence of an α-keto acid and a peroxidative substance in step 2 can be performed under any reaction condition as long as a dye is formed. For example, the reaction is performed at 10 to 50° C., preferably 20 to 40° C., for 1 minute to 3 hours, preferably 2.5 minutes to 1 hour. The concentration of the α-keto acid in this reaction is not particularly limited as long as the influence of a peroxide can be suppressed. The concentration is, for example, 0.001 to 20 g/L.

The method for measuring the absorbance of the formed dye in step 3 can be any method capable of measuring absorbance. Examples thereof include a measurement method using a spectrophotometer.

The hydrogen peroxide-forming reagent used in step 1 is a reagent that reacts with the component to form hydrogen peroxide. Examples thereof include (A) a reagent that directly converts the component into hydrogen peroxide [hereinafter referred to as reagent (A)], (B) a reagent that indirectly converts the component into hydrogen peroxide [hereinafter referred to as reagent (B)], (C) a reagent that directly generates hydrogen peroxide from the component [hereinafter referred to as reagent (C)], and (D) a reagent that indirectly generates hydrogen peroxide from the component [hereinafter referred to as reagent (D)].

The reagent (A) is a reagent that directly converts the component to be measured in the sample into hydrogen peroxide. The component to be measured to which the reagent (A) is applied is, for example, an oxidase substrate. Examples of the reagent (A) include a reagent comprising an oxidase for the component to be measured. Specific examples of combinations of the component to be measured and the reagent (A) are shown in Table 1.

TABLE 1

| Analyte Component | Reagent (A) |
| --- | --- |
| Choline | Reagent comprising choline oxidase |
| Urate | Reagent comprising uricase (urate oxidase) |

TABLE 1-continued

| Analyte Component | Reagent (A) |
| --- | --- |
| Glucose | Reagent comprising glucose oxidase |
| Pyruvic acid | Reagent comprising pyruvate oxidase |
| Lactic acid | Reagent comprising lactate oxidase |
| Glycerol | Reagent comprising glycerol oxidase |
| Sarcosine | Reagent comprising sarcosine oxidase |
| Acyl CoA | Reagent comprising acyl CoA oxidase |
| Xanthine | Reagent comprising xanthine oxidase |
| Fructosyl amino acid | Reagent comprising fructosyl amino acid oxidase |
| Fructosyl peptide | Reagent comprising fructosyl peptide oxidase |
| L-aspartic acid | Reagent comprising L-aspartate oxidase |
| Free cholesterol | Reagent comprising cholesterol oxidase |
| Free cholesterols in various lipoproteins | Reagent comprising cholesterol oxidase |
| Fructosyl dipeptide | Reagent comprising fructosyl peptide oxidase |
| Fructosyl amino acid | Reagent comprising fructosyl amino acid oxidase |

In this table, various lipoproteins refer to HDL, LDL, VLDL, IDL, remnant lipoprotein, sdLDL, etc. The same holds true for the description below.

The oxidase substrate to be measured can be induced through a plurality of reactions. In this case, a component to be measured is converted into an oxidase substrate through a plurality of reactions. The oxidase substrate is then reacted with the oxidase to form hydrogen peroxide. Table 2 shows examples of combinations of substance that is to be converted into oxidase substrate; oxidase substrate; and oxidase. Table 2.

TABLE 2

| Substance that is converted into oxidase substrate | Oxidase substrate | Oxidase |
| --- | --- | --- |
| Creatine | Sarcosine | Sarcosine oxidase |
| Sialic acid | Pyruvic acid | Pyruvate oxidase |
| Total cholesterol | Free cholesterol | Cholesterol oxidase |
| Cholesterols in various lipoproteins | Free cholesterol | Cholesterol oxidase |
| Total cholesterol ester | Free cholesterol | Cholesterol oxidase |
| Cholesterol esters in various lipoproteins | Free cholesterol | Cholesterol oxidase |
| Total triglyceride | Glycerol-3-phosphate | Glycerol-3-phosphate oxidase |
| Triglycerides in various lipoproteins | Glycerol-3-phosphate | Glycerol-3-phosphate oxidase |
| Total triglyceride | Glycerol | Glycerol oxidase |
| Triglycerides in various lipoproteins | Glycerol | Glycerol oxidase |
| Starch | Glucose | Glucose oxidase |
| Maltose | Glucose | Glucose oxidase |
| Phospholipid | Choline | Choline oxidase |
| Free fatty acid | Acyl CoA | Acyl CoA oxidase |
| Inorganic phosphoric acid | Xanthine | Xanthine oxidase |
| Glycoalbumin | Ketoamine | Ketoamine oxidase |
| Fructosyl hexapeptide | Fructosyl amino acid or fructosyl peptide | Fructosyl amino acid oxidase or fructosyl peptide oxidase |
| Hemoglobin A1c | Fructosyl amino acid or fructosyl peptide | Fructosyl amino acid oxidase or fructosyl peptide oxidase |

In this context, the total cholesterol means the sum of free cholesterols and cholesterol esters in all lipoproteins. The cholesterols in various lipoproteins mean the sum of free cholesterols and cholesterol esters in various lipoproteins. The total cholesterol ester means cholesterol esters in all lipoproteins.

The reagent (B) is a reagent that indirectly converts the component to be measured in the sample into hydrogen peroxide. Examples of the component to be measured to which the reagent (B) is applied include an enzyme substrate that is converted into hydrogen peroxide through two or more enzyme reactions. Examples of the reagent (B) include a reagent comprising the following components: (i) an enzyme that reacts with the substrate; (ii) an enzyme or a combination of an enzyme and a substrate thereof that converts a substance formed by the reaction of the substrate with the enzyme of (i) into a substance for which the corresponding oxidase exists; and (iii) the oxidase. Combinations of the component and the reagent (B) are shown in Table 3.

TABLE 3

| Analyte Component | Reagent (B) |
| --- | --- |
| Creatinine | Reagent comprising creatininase, creatinase, and sarcosine oxidase |
| Creatine | Reagent comprising creatinase and sarcosine oxidase |
| Sialic acid | Reagent comprising neuraminidase, N-acetylneuraminic acid aldolase, pyruvate oxidase, and inorganic phosphorus |
| Total cholesterol | Reagent comprising cholesterol ester hydrolase and cholesterol oxidase |
| Cholesterols in various lipoproteins | Reagent comprising cholesterol ester hydrolase and cholesterol oxidase |
| Total cholesterol ester | Reagent comprising cholesterol ester hydrolase and cholesterol oxidase |
| Cholesterol esters in various lipoproteins | Reagent comprising cholesterol ester hydrolase and cholesterol oxidase |
| Total triglyceride | Reagent comprising lipoprotein lipase, glycerol kinase, and glycerol-3-phosphate oxidase |
| Triglycerides in various lipoproteins | Reagent comprising lipoprotein lipase, glycerol kinase, and glycerol-3-phosphate oxidase |
| Total triglyceride | Reagent comprising lipoprotein lipase and glycerol oxidase |
| Triglycerides in various lipoproteins | Reagent comprising lipoprotein lipase and glycerol oxidase |
| Starch | Reagent comprising amylase and glucose oxidase |
| Maltose | Reagent comprising amylase and glucose oxidase |
| Phospholipid | Reagent comprising phospholipase D and choline oxidase |
| Free fatty acid | Reagent comprising acyl CoA synthetase and acyl CoA oxidase |
| Inorganic phosphoric acid | Reagent comprising inosine, purine nucleoside phosphorylase, and xanthine oxidase |
| Glycoalbumin | Reagent comprising protease and ketoamine oxidase |
| Fructosyl hexapeptide | Reagent comprising protease and fructosyl amino acid oxidase or fructosyl peptide oxidase |
| Hemoglobin A1c | Reagent comprising protease and fructosyl amino acid oxidase or fructosyl peptide oxidase |

The reagent (C) is a reagent that directly generates hydrogen peroxide from the component to be measured. Examples of the component to be measured to which the reagent (C) is applied include an oxidase that generates hydrogen peroxide. Examples of the reagent (C) include a reagent comprising a substrate of the oxidase. Specific examples of combinations of the component and the reagent (C) are shown in Table 4.

TABLE 4

| component | Reagent (C) |
| --- | --- |
| Choline oxidase | Reagent comprising choline |
| Uricase (urate oxidase) | Reagent comprising urate |
| Glucose oxidase | Reagent comprising glucose |
| Pyruvate oxidase | Reagent comprising pyruvic acid |
| Lactate oxidase | Reagent comprising lactic acid |
| Glycerol oxidase | Reagent comprising glycerol |
| Sarcosine oxidase | Reagent comprising sarcosine |
| Acyl CoA oxidase | Reagent comprising acyl CoA |
| Xanthine oxidase | Reagent comprising xanthine |
| Fructosyl amino acid oxidase | Reagent comprising fructosyl amino acid |
| Fructosyl peptide oxidase | Reagent comprising fructosyl peptide |
| L-aspartate oxidase | Reagent comprising L-aspartic acid |
| Monoamine oxidase | Reagent comprising allylamine |
| Polyamine oxidase | Reagent comprising polyamine |
| Cholesterol oxidase | Reagent comprising free cholesterol |
| Cholesterol oxidase | Reagent comprising free cholesterols in various lipoproteins |

The reagent (D) is a reagent that indirectly generates hydrogen peroxide from the component to be measured. Examples of the component to be measured to which the reagent (D) is applied include an enzyme that generates hydrogen peroxide through two or more reactions, and the like. Examples of the reagent (D) include a reagent the following components: (i) a substrate of an enzyme; (ii) an enzyme or a combination of an enzyme and a substrate thereof that converts a substance formed by a reaction of the enzyme in (i) with the substrate of (i) into a substance for which the corresponding oxidase exists; and (iii) the oxidase. Specific examples of combinations of the component to be measured and the reagent (D) are shown in Table 5.

TABLE 5

| Analyte Component | Reagent (D) |
| --- | --- |
| Choline esterase | Reagent comprising 2,4-dimethoxybenzoylcholine and choline oxidase |
| Guanase | Reagent comprising guanine, xanthine oxidase, and uricase |
| GOT | Reagent comprising L-aspartic acid, α-ketoglutaric acid, oxaloacetic acid decarboxylase, pyruvate oxidase, and inorganic phosphorus |
| GPT | Reagent comprising L-alanine, α-ketoglutaric acid, pyruvate oxidase, and inorganic phosphorus |
| N-acetylglucosaminidase | Reagent comprising p-nitrophenyl-N-acetylglucosaminide and N-acetylglucosamine oxidase |
| Pyruvate kinase | Reagent comprising phosphoenolpyruvate, ADP, and pyruvate oxidase |

In the present invention, the oxidative-coloring chromogen reacts with hydrogen peroxide in the presence of a peroxidative substance to form a dye. Examples of the peroxidative substance include peroxidase. Examples of the oxidative-coloring chromogen include an oxidation coupling-type chromogen, and a leuco chromogen. A leuco chromogen is preferred.

The leuco chromogen is a substance that is converted by itself into a dye in the presence of hydrogen peroxide and a peroxidative substance.

Examples of the leuco chromogen include a phenothiazine chromogen, triphenylmethane chromogen, diphenylamine chromogen, o-phenylenediamine, hydroxypropionic acid, diaminobenzidine, and tetramethylbenzidine. A phenothiazine chromogen is preferred.

Examples of the phenothiazine chromogen include 10-N-carboxymethylcarbamoyl-3,7-bis(dimethylamino)-10H-phenothiazine (CCAP), 10-N-methylcarbamoyl-3,7-bis(dimethylamino)-10H-phenothiazine (MCDP), and 10-N-(carboxymethylaminocarbonyl)-3,7-bis(dimethylamino)-10H-phenothiazine sodium salt (DA-67). Among these phenothiazine chromogens, 10-N-(carboxymethylaminocarbonyl)-3,7-bis(dimethylamino)-10H-phenothiazine sodium salt (DA-67) is particularly preferred.

Examples of the triphenylmethane chromogen include N,N,N',N',N'',N''-hexa(3-sulfopropyl)-4,4',4''-triaminotriphenylmethane (TPM-PS).

Examples of the diphenylamine chromogen include N-(carboxymethylaminocarbonyl)-4,4'-bis(dimethylamino)diphenylamine sodium salt (DA-64), 4,4'-bis(dimethylamino)diphenylamine, and bis[3-bis(4-chlorophenyl)methyl-4-dimethylaminophenyl]amine (BCMA).

The oxidative coupling-type chromogen is a combination of two compounds that forms a dye by oxidative coupling in the presence of hydrogen peroxide and a peroxidative substance. Examples of the combination of two compounds include a combination of a coupler and an aniline (the Trinder reagent) and a combination of a coupler and a phenol.

Examples of the coupler include 4-aminoantipyrine (4-AA) and 3-methyl-2-benzothiazolinone hydrazine.

Examples of the aniline include N-(3-sulfopropyl)aniline, N-ethyl-N-(2-hydroxy-3-sulfopropyl)-3-methylaniline (TOOS), N-ethyl-N-(2-hydroxy-3-sulfopropyl)-3,5-dimethylaniline (MAOS), N-ethyl-N-(2-hydroxy-3-sulfopropyl)-3,5-dimethoxyaniline (DAOS), N-ethyl-N-(3-sulfopropyl)-3-methylaniline (TOPS), N-(2-hydroxy-3-sulfopropyl)-3,5-dimethoxyaniline (HDAOS), N,N-dimethyl-3-methylaniline, N,N-bis(3-sulfopropyl)-3,5-dimethoxyaniline, N-ethyl-N-(3-sulfopropyl)-3-methoxyaniline, N-ethyl-N-(3-sulfopropyl)aniline, N-ethyl-N-(3-sulfopropyl)-3,5-dimethoxyaniline, N-(3-sulfopropyl)-3,5-dimethoxyaniline, N-ethyl-N-(3-sulfopropyl)-3,5-dimethylaniline, N-ethyl-N-(2-hydroxy-3-sulfopropyl)-3-methoxyaniline, N-ethyl-N-(2-hydroxy-3-sulfopropyl)aniline, N-ethyl-N-(3-methylphenyl)-N'-succinylethylenediamine (EMSE), N-ethyl-N-(3-methylphenyl)-N'-acetylethylenediamine, and N-ethyl-N-(2-hydroxy-3-sulfopropyl)-4-fluoro-3,5-dimethoxyaniline (F-DAOS).

Examples of the phenol include phenol, 4-chlorophenol, 3-methylphenol, and 3-hydroxy-2,4,6-triiodobenzoic acid (HTIB).

In the present invention, the peroxide is a substance that has a positive influence on the measuring method of the present invention. Examples thereof include a peroxide derived from a surfactant capable of forming peroxide. In the present invention, the peroxide can be a peroxide derived from the sample or can be a peroxide derived from a measuring reagent. Examples of the surfactant capable of forming a peroxide include a polyoxyalkylene surfactant. Examples of the polyoxyalkylene surfactant include a polyoxyethylene surfactant, a polyoxypropylene surfactant, and a polyoxybutylene surfactant. Examples of the polyoxyalkylene surfactant include a nonionic surfactant, a cationic surfactant, an anionic surfactant, and an amphoteric surfactant. A nonionic surfactant is preferred. Examples of the nonionic surfactant include polyoxyethylene alkyl ether, polyoxyethylene alkenyl ether, polyoxyethylene alkylaryl ether, polyoxyethylene polyoxypropylene alkyl ether, polyoxyethylene polyoxypropylene alkenyl ether, polyoxyethylene polyoxypropylene alkylaryl ether, and polyoxyethylenepolyoxypropylene copolymers.

The peroxide can be detected, measured, or quantified on the basis of an index for fat oxidation, such as peroxide values, carbonyl values, or thiobarbituric acid values.

The α-keto acid according to the present invention is not particularly limited as long as the measuring method of the present invention can be carried out. Examples thereof include pyruvic acid, oxaloacetic acid, α-ketoglutaric acid, and oxalic acid. Pyruvic acid, oxaloacetic acid, and α-ketoglutaric acid are preferred, and pyruvic acid is particularly preferred. The α-keto acid according to the present invention can be in a salt form. Examples of the salt include sodium salt, potassium salt, ammonium salt, and calcium salt.

The concentration of the α-keto acid used in the measuring method of the present invention is not particularly limited as long as the measuring method of the present invention is carried out. The concentration is, for example, 0.001 to 20 g/L.

The reaction of the component to be measured with the hydrogen peroxide-forming reagent in the measuring method of the present invention is preferably performed in an aqueous medium. Alternatively, the reaction of the component to be measured with the hydrogen peroxide-forming reagent can be performed in the presence of a stabilizer, an antiseptic, an interfering substance-eliminating agent, a reaction accelerator, and the like.

Examples of the aqueous medium include a deionized water, a distilled water, and a buffer solution. A buffer solution is preferred. The pH of the buffer solution is 4.0 to 10.0, preferably 6.0 to 8.0. Examples of the buffer used in the buffer solution include a phosphate buffer, a borate buffer, and a Good's buffer.

Examples of the Good's buffer include 2-morpholinoethanesulfonic acid (MES), tris(hydroxymethyl)aminomethane (Tris), bis(2-hydroxyethyl)iminotris(hydroxymethyl)methane (Bis-Tris), N-(2-acetamido)iminodiacetic acid (ADA), piperazine-N,N'-bis(2-ethanesulfonic acid) (PIPES), N-(2-acetamido)-2-aminoethanesulfonic acid (ACES), 3-morpholino-2-hydroxypropanesulfonic acid (MOPSO), N,N-bis(2-hydroxyethyl)-2-aminoethanesulfonic acid (BES), 3-morpholinopropanesulfonic acid (MOPS), N-[tris(hydroxymethyl)methyl]-2-aminoethanesulfonic acid (TES), 2-[4-(2-hydroxyethyl)-1-piperazinyl]ethanesulfonic acid (HEPES), 3-[N,N-bis(2-hydroxyethyl)amino]-2-hydroxypropanesulfonic acid (DIPSO), N-[tris(hydroxymethyl)methyl]-2-hydroxy-3-aminopropanesulfonic acid (TAPSO), piperazine-N,N'-bis(2-hydroxypropanesulfonic acid) (POPSO), 3-[4-(2-hydroxyethyl)-1-piperazinyl]-2-hydroxypropanesulfonic acid (HEPPSO), 3-[4-(2-hydroxyethyl)-1-piperazinyl]propanesulfonic acid [(H)EPPS], N-[tris(hydroxymethyl)methyl]glycine (Tricine), N,N-bis(2-hydroxyethyl)glycine (Bicine), N-tris(hydroxymethyl)methyl-3-aminopropanesulfonic acid (TAPS), N-cyclohexyl-2-aminoethanesulfonic acid (CHES), N-cyclohexyl-3-amino-2-hydroxypropanesulfonic acid (CAPSO), and N-cyclohexyl-3-aminopropanesulfonic acid (CAPS).

The concentration of the buffer solution is not particularly limited as long as the concentration is suitable for the measurement. The concentration is preferably 0.001 to 2.0 mol/L, more preferably 0.005 to 1.0 mol/L.

Examples of the stabilizer include ethylenediaminetetraacetic acid (EDTA), sucrose, calcium chloride, potassium ferrocyanide, and bovine serum albumin (BSA). Examples of the antiseptic include sodium azide and an antibiotic. Examples of the interfering substance-eliminating agent include ascorbate oxidase for eliminating the influence of ascorbate. Examples of the reaction accelerator include: an enzyme such as colipase and phospholipase; and a salt such as sodium sulfate and sodium chloride.

(2) Reagent and Kit for Measurement of Component to be Measured

The reagent for measurement of a component to be measured in a sample according to the present invention is a reagent that is used in the measurement method of the present invention and comprises a hydrogen peroxide-forming reagent, an α-keto acid, a peroxidative substance, and an oxidative-coloring chromogen.

Specific embodiments of the reagent for measurement of the present invention will be shown below.

Reagent 1 for Measurement

A reagent comprising a hydrogen peroxide-forming reagent, an α-keto acid, a peroxidative substance, and a leuco chromogen.

Reagent 2 for Measurement

A reagent comprising a hydrogen peroxide-forming reagent, an α-keto acid, a peroxidative substance, and a coupling-type chromogen.

The reagent for measurement of a component to be measured in a sample according to the present invention can be stored, distributed, and used in a kit form. The kit for measurement of the present invention is used in the measurement method of the present invention. Examples thereof include a two-reagent kit and a three-reagent kit. A two-reagent kit is preferred.

The kit for measurement of the present invention can be a two-reagent kit comprising a leuco chromogen as the oxidative-coloring chromogen. In this case, the leuco chromogen can be comprised in a first reagent, and a peroxidative substance can be comprised in a second reagent, respectively. In addition, a hydrogen peroxide-forming reagent and an α-keto acid can be comprised in one or both of the first and the second reagent(s).

The kit for measurement of the present invention can be a two-reagent kit comprising an oxidative coupling-type chromogen as the oxidative-coloring chromogen. In this case, a coupler can be comprised in a first reagent, and an aniline derivative or a phenol derivative can be comprised in a second reagent, respectively. In addition, a peroxidative substance, a hydrogen peroxide-forming reagent and an α-keto acid can be comprised in one or both of the first and the second reagent(s).

Specific embodiments of the kit for measurement of the present invention will be shown below.

Kit 1 for Measurement
First Reagent
A reagent comprising a leuco chromogen and an α-keto acid.
Second Reagent
A reagent comprising a peroxidative substance and a hydrogen peroxide-forming reagent.

Kit 2 for Measurement
First Reagent
A reagent comprising a leuco chromogen, an α-keto acid, and a hydrogen peroxide-forming reagent.
Second Reagent
A reagent comprising a peroxidative substance and a hydrogen peroxide-forming reagent.

Kit 3 for Measurement
First Reagent
A reagent comprising a leuco chromogen, an α-keto acid, and a hydrogen peroxide-forming reagent.
Second Reagent
A reagent comprising a peroxidative substance, an α-keto acid, and a hydrogen peroxide-forming reagent.

Kit 4 for Measurement
First Reagent
A reagent comprising a peroxidative substance and an α-keto acid.
Second Reagent
A reagent comprising a leuco chromogen and a hydrogen peroxide-forming reagent.

Kit 5 for Measurement
First Reagent
A reagent comprising a peroxidative substance, an α-keto acid, and a hydrogen peroxide-forming reagent.
Second Reagent
A reagent comprising a leuco chromogen and a hydrogen peroxide-forming reagent.

Kit 6 for Measurement
First Reagent
A reagent comprising a peroxidative substance, an α-keto acid, and a hydrogen peroxide-forming reagent.
Second Reagent
A reagent comprising a leuco chromogen, an α-keto acid, and a hydrogen peroxide-forming reagent.

Kit 7 for Measurement
First Reagent
A reagent comprising a coupler and an α-keto acid.
Second Reagent
A reagent comprising an aniline derivative or a phenol derivative, a peroxidative substance, and a hydrogen peroxide-forming reagent.

Kit 8 for Measurement
First Reagent
A reagent comprising an aniline derivative or a phenol derivative, and an α-keto acid.
Second Reagent
A reagent comprising a coupler, a peroxidative substance, and a hydrogen peroxide-forming reagent.

Kit 9 for Measurement
First Reagent
A reagent comprising a coupler, an α-keto acid, and a hydrogen peroxide-forming reagent.
Second Reagent
A reagent comprising an aniline derivative or a phenol derivative, a peroxidative substance, and a hydrogen peroxide-forming reagent.

Kit 10 for Measurement
First Reagent
A reagent comprising an aniline derivative or a phenol derivative, an α-keto acid, and a hydrogen peroxide-forming reagent.
Second Reagent
A reagent comprising a coupler, a peroxidative substance, and a hydrogen peroxide-forming reagent.

Kit 11 for Measurement
First Reagent
A reagent comprising a coupler, an α-keto acid, and a hydrogen peroxide-forming reagent.

Second Reagent

A reagent comprising an aniline derivative or a phenol derivative, a peroxidative substance, an α-keto acid, and a hydrogen peroxide-forming reagent.

Kit 12 for Measurement
First Reagent

A reagent comprising an aniline derivative or a phenol derivative, an α-keto acid, and a hydrogen peroxide-forming reagent.

Second Reagent

A reagent comprising a coupler, a peroxidative substance, an α-keto acid, and a hydrogen peroxide-forming reagent.

Examples of the hydrogen peroxide-forming reagent in the reagent and the kit for measurement of the present invention include the reagents (A) to (D) shown above. Examples of the α-keto acid, the peroxidative substance, and the oxidative-coloring chromogen in the reagent and the kit for measurement of the present invention include those described above in the paragraph (1).

The reagent and the kit for measurement of the present invention can further comprise a stabilizer, an antiseptic, an interfering substance-eliminating agent, a reaction accelerator, and the like, if necessary. Examples of the stabilizer, the antiseptic, the interfering substance-eliminating agent, and the reaction accelerator include those described above in the paragraph (1).

(3) Method for Suppressing Influence of Peroxide

The method for suppressing an influence of a peroxide according to the present invention is a method for suppressing the influence of a peroxide on a method for measuring a component to be measured in a sample by converting the component to be measured in the sample into hydrogen peroxide and reacting the formed hydrogen peroxide with an oxidative-coloring chromogen, and the suppression method comprises reacting the formed hydrogen peroxide with the oxidative-coloring chromogen in the presence of an α-keto acid.

Examples of the sample, the component to be measured, the oxidative-coloring chromogen, and the α-keto acid in the method for suppressing the influence of a peroxide according to the present invention include the sample, the component to be measured, the oxidative-coloring chromogen, and the α-keto acid, respectively, described above. Also, examples of the peroxide whose influence is suppressed by the suppression method of the present invention include the peroxide described above.

The method for suppressing the influence of a peroxide according to the present invention gives an accurate measurement of the component to be measured in the sample.

In the present invention, the suppression of the influence of a peroxide can be evaluated, for example, by the following steps:

Step 1: the step of preparing a reagent comprising an α-keto acid [hereinafter referred to as reagent(+)] and a reagent comprising no α-keto acid [hereinafter referred to as reagent (−)];

Step 2: the step of reacting a sample with the reagent(+) and measuring the absorbance of the resulting dye;

Step 3: the step of reacting the sample with the reagent (−) and measuring the absorbance of the resulting dye; and Step 4: the step of comparing the absorbance measured in step 2 with the absorbance measured in step 3.

When the absorbance measured in step 2, i.e., the absorbance obtained using the reagent(+) is lower than the absorbance measured in step 3, i.e., the absorbance obtained using the reagent(−) in the comparison of step 4, it can be evaluated that the α-keto acid suppresses the influence of a peroxide.

Hereinafter, the present invention will be described more specifically with reference to Examples. However, these Examples do not limit the scope of the present invention by any means.

Reagents and enzymes from the following manufacturers were used in these Examples, Comparative Examples, and Test Examples.

MES (manufactured by Dojindo Laboratories), Bis-Tris (manufactured by Dojindo Laboratories), ADA (manufactured by Dojindo Laboratories), peroxidase (POD; manufactured by Toyobo Co., Ltd.), sodium pyruvate (manufactured by Kanto Chemical Co., Inc.), α-ketoglutaric acid (manufactured by Kanto Chemical Co., Inc.), oxaloacetic acid (manufactured by Kanto Chemical Co., Inc.), DA-67 (manufactured by Wako Pure Chemical Industries, Ltd.), 4-AA (manufactured by Saikyo Kasei Co., Ltd.), EMSE (manufactured by Daito Chemix Corp.), calcium chloride dihydrate (manufactured by Wako Pure Chemical Industries, Ltd.), sodium sulfate (manufactured by Kanto Chemical Co., Inc.), sodium nitrate (manufactured by Kanto Chemical Co., Inc.), decyl trimethyl ammonium bromide (C10TMA; manufactured by Tokyo Chemical Industry Co., Ltd.), 1-dodecylpyridinium chloride (manufactured by Tokyo Chemical Industry Co., Ltd.), glucose (manufactured by Merck KGaA), fructosyl VHLTPE (fructosyl hexapeptide; manufactured by Peptide Institute, Inc.), glucose oxidase (GOD; manufactured by Toyobo Co., Ltd.), thermolysin (protease; manufactured by Amano Enzyme Inc.), Actinase E (protease; manufactured by Kaken Pharmaceutical Co., Ltd.), FPOX-CE (fructosyl peptide oxidase; manufactured by Kikkoman Corp.), FPOX-CET (fructosyl peptide oxidase; manufactured by Kikkoman Corp.), Dispanol TOC (polyoxyethylene tridecyl ether; manufactured by NOF Corp.), and Nonion E230 (polyoxyethylene oleyl ether; manufactured by NOF Corp.).

Example 1

(1) Kit for Measurement of Glucose Comprising Pyruvic Acid

A kit for measurement of glucose (kit A) having the following composition was prepared:

First Reagent

| MES (pH 6.25) | 20 mmol/L |
| --- | --- |
| DA-67 | 50 μmol/L |
| Sodium pyruvate | 5 g/L |

Second Reagent

| MES (pH 6.25) | 20 mmol/L |
| --- | --- |
| POD | 10 kU/L |
| GOD | 5 kU/L |

(2) Kit for Measurement of Glucose Comprising No Pyruvic Acid

A kit for measurement of glucose (kit a) having the following composition was prepared:

First Reagent

| MES (pH 6.25) | 20 mmol/L |
| --- | --- |
| DA-67 | 50 μmol/L |

Second Reagent

| MES (pH 6.25) | 20 mmol/L |
|---|---|
| POD | 10 kU/L |
| GOD | 5 kU/L |

(3) Preparation of Peroxide-Containing Sample

The following four samples were prepared:

Sample 1: an aqueous solution comprising glucose and Dispanol TOC at concentrations of 90 μmol/L and 0%, respectively.

Sample 2: an aqueous solution comprising glucose and Dispanol TOC at concentrations of 90 μmol/L and 0.25%, respectively.

Sample 3: an aqueous solution comprising glucose and Dispanol TOC at concentrations of 90 μmol/L and 0.5%, respectively.

Sample 4: an aqueous solution comprising glucose and Dispanol TOC at concentrations of 90 μmol/L and 1%, respectively.

The Dispanol TOC is a polyoxyethylene surfactant and is a source for peroxide formation. The samples 1 to 4 contain a larger amount of peroxides depending on the Dispanol TOC concentration.

(4) Evaluation of Effect of Suppressing Influence of Peroxides on Hydrogen Peroxide Quantification System by Pyruvic Acid The sample 1 (1.5 μL) prepared in the paragraph (3) was reacted at 37° C. for 5 minutes with the first reagent (150 μL) in the kit A prepared in the paragraph (1). The absorbance (E1) was measured at a main wavelength of 660 nm and a sub-wavelength of 800 nm. Subsequently, the second reagent (50 μL) of the kit A was added thereto and further reaction was continued at 37° C. for 5 minutes. The absorbance (E2) was measured at a main wavelength of 660 nm and a sub-wavelength of 800 nm. The measurement was performed using Hitachi H7180. The absorbance (E1) was subtracted from the absorbance (E2) to determine the reaction absorbance ($E_{1A}$) for the sample 1.

Subsequently, the same measurement as above was performed using saline instead of the sample 1 to determine blank absorbance ($E_{blank}$). The blank absorbance ($E_{blank}$) was subtracted from the reaction absorbance ($E_{1A}$) for the sample 1 to determine absorbance ($\Delta E_{1A}$) for the sample 1.

This sequence of operations performed for the sample 1 was also performed for each of the samples 2 to 4 to determine measurement values of absorbance ($\Delta E_{2A}$) for the sample 2, absorbance ($\Delta E_{3A}$) for the sample 3, and absorbance ($\Delta E_{4A}$) for the sample 4. The relative values of the absorbances ($\Delta E_{2A}$ to $\Delta E_{4A}$) for the samples 2 to 4 to the absorbance ($\Delta E_{1A}$) for the sample 1 as 100 are shown in Table 6.

In addition, relative values of respective absorbances ($\Delta E_{1a}$ to $\Delta E_{4a}$) for the samples 1 to 4 were determined in the same way as above except that the kit a prepared in the paragraph (2) was used instead of the kit A prepared in the paragraph (1). The relative values of the absorbances ($\Delta E_{2a}$ to $\Delta E_{4a}$) for the samples 2 to 4 to the absorbance ($\Delta E_{1a}$) for the sample 1 as 100 are shown in Table 6.

TABLE 6

| Sample | | Relative value of absorbance | |
|---|---|---|---|
| Sample No. | Dispanol TOC (%) | Kit a | Kit A |
| Sample 1 | 0 | 100 | 100 |
| Sample 2 | 0.25 | 123 | 106 |
| Sample 3 | 0.5 | 159 | 117 |
| Sample 4 | 1 | 203 | 124 |

As is evident from Table 6, in the glucose quantification system using the leuco chromogen DA-67, the measurement using the kit A comprising pyruvic acid significantly suppressed the influence of Dispanol TOC-derived peroxides, compared with the measurement using the kit a comprising no pyruvic acid, demonstrating that the measurement using the kit A gives a more accurate measurement of glucose.

Example 2

(1) Kit for Measurement of Glucose Comprising Pyruvic Acid

A kit for measurement of glucose (kit B) having the following composition was prepared:

First Reagent

| MES (pH 6.25) | 20 mmol/L |
|---|---|
| EMSE | 0.3 g/L |
| Sodium pyruvate | 5 g/L |

Second Reagent

| MES (pH 6.25) | 20 mmol/L |
|---|---|
| POD | 10 kU/L |
| 4-AA | 0.1 g/L |
| GOD | 5 kU/L |

(2) Kit for Measurement of Glucose Comprising No Pyruvic Acid

A kit for glucose measurement (kit b) having the following composition was prepared:

First Reagent

| MES (pH 6.25) | 20 mmol/L |
|---|---|
| EMSE | 0.3 g/L |

Second Reagent

| MES (pH 6.25) | 20 mmol/L |
|---|---|
| POD | 10 kU/L |
| 4-AA | 0.1 g/L |
| GOD | 5 kU/L |

(3) Preparation of Peroxide-Containing Sample

The samples 1 to 4 prepared in Example 1 were used.

(4) Evaluation of Effect of Suppressing Influence of Peroxides on Hydrogen Peroxide Quantification System by Pyruvic Acid The sample 1 (15 μL) prepared in the paragraph (3) was reacted at 37° C. for 5 minutes with the first reagent (150 μL) in the kit A prepared in the paragraph (1). The absorbance (E1) was measured at a main wavelength of 660 nm and a sub-wavelength of 800 nm. Subsequently, the second reagent (50 μL) of the kit A was added thereto and further reacted at 37° C. for 5 minutes. The absorbance (E2) was measured at a main wavelength of 546 nm and a sub-wavelength of 800 nm. The measurement was performed using Hitachi H7180. The absorbance (E1) was subtracted from the absorbance (E2) to determine the reaction absorbance ($E_{1B}$) for the sample 1.

The same measurement as above was performed using saline instead of the sample 1 to determine blank absorbance ($E_{blank}$). The blank absorbance ($E_{blank}$) was subtracted from the reaction absorbance ($E_{1B}$) for the sample 1 to determine absorbance ($\Delta E_{1B}$) for the sample 1.

This sequence of operations performed for the sample 1 was also performed for each of the samples 2 to 4 to determine measurement values of absorbance ($\Delta E_{2B}$) for the sample 2, absorbance ($\Delta E_{3B}$) for the sample 3, and absorbance ($\Delta E_{4B}$) for the sample 4. The relative values of the absorbances ($\Delta E_{2B}$ to $\Delta E_{4B}$) for the samples 2 to 4 to the absorbance ($\Delta E_{1B}$) for the sample 1 as 100 are shown in Table 7.

In addition, relative values of respective absorbances ($\Delta E_{1b}$ to $\Delta E_{4b}$) for the samples 1 to 4 were determined in the same way as above except that the kit b prepared in the paragraph (2) was used instead of the kit B prepared in the paragraph (1). The relative values of the absorbances ($\Delta E_{2b}$ to $\Delta E_{4b}$) for the samples 2 to 4 to the absorbance ($\Delta E_{1b}$) for the sample 1 as 100 are shown in Table 7.

TABLE 7

| Sample | | Relative value of absorbance | |
|---|---|---|---|
| Sample No. | Dispanol TOC (%) | Kit b | Kit B |
| Sample 1 | 0 | 100 | 100 |
| Sample 2 | 0.25 | 130 | 107 |
| Sample 3 | 0.5 | 152 | 110 |
| Sample 4 | 1 | 192 | 115 |

As is evident from Table 7, in the glucose quantification system using the coupling-type chromogen of the combination of 4-AA and EMSE, the measurement using the kit B comprising pyruvic acid significantly suppressed the influence of Dispanol TOC-derived peroxides, compared with the measurement using the kit b comprising no pyruvic acid, demonstrating that the measurement using the kit B gives a more accurate measurement of glucose.

Example 3

(1) Kit for Measurement of Fructosyl VHLTPE Comprising Pyruvic Acid

A kit for measurement of fructosyl VHLTPE (kit C) having the following composition was prepared:
First Reagent

| Bis-Tris (pH 7.0) | 10 mmol/L |
|---|---|
| Calcium chloride dihydrate | 10 mmol/L |
| Sodium sulfate | 7.5 mmol/L |
| C10TMA | 17 g/L |
| DA-67 | 20 μmol/L |
| Thermolysin | 1200 kU/L |
| Sodium pyruvate | 5 g/L |

Second Reagent

| ADA (pH 7.0) | 50 mmol/L |
|---|---|
| POD | 120 kU/L |
| FPOX-CE | 12 kU/L |

(2) Kit for Measurement of Fructosyl VHLTPE Comprising No Pyruvic Acid

A kit for measurement of fructosyl VHLTPE (kit c) having the following composition was prepared:
First Reagent

| Bis-Tris (pH 7.0) | 10 mmol/L |
|---|---|
| Calcium chloride dihydrate | 10 mmol/L |
| Sodium sulfate | 7.5 mmol/L |
| C10TMA | 17 g/L |
| DA-67 | 20 μmol/L |
| Thermolysin | 1200 kU/L |

Second Reagent

| ADA (pH 7.0) | 50 mmol/L |
|---|---|
| POD | 120 kU/L |
| FPOX-CE | 12 kU/L |

(3) Preparation of Peroxide-Containing Sample

The following four samples were prepared:
Sample 1: an aqueous solution comprising fructosyl VHLTPE and Dispanol TOC at concentrations of 18 μmol/L and 0%, respectively.
Sample 2: an aqueous solution comprising fructosyl VHLTPE and Dispanol TOC at concentrations of 18 μmol/L and 0.05%, respectively.
Sample 3: an aqueous solution comprising fructosyl VHLTPE and Dispanol TOC at concentrations of 18 μmol/L and 0.1%, respectively.
Sample 4: an aqueous solution comprising fructosyl VHLTPE and Dispanol TOC at concentrations of 18 μmol/L and 0.2%, respectively.

The Dispanol TOC is a polyoxyethylene surfactant and is a source for peroxide formation. The samples 1 to 4 contain a larger amount of peroxides depending on the Dispanol TOC concentration.

(4) Evaluation of Effect of Suppressing Influence of Peroxides on Hydrogen Peroxide Quantification System by Pyruvic Acid The sample 1 (9.6 μL) prepared in the paragraph (3) was reacted at 37° C. for 5 minutes with the first reagent (120 μL) in the kit C prepared in the paragraph (1). The absorbance (E1) was measured at a main wavelength of 660 nm and a sub-wavelength of 800 nm. Subsequently, the second reagent (40 μL) of the kit C was added thereto and further reacted at 37° C. for 5 minutes. The absorbance (E2) was measured at a main wavelength of 660 nm and a sub-wavelength of 800 nm. The measurement was performed using Hitachi H7180. The absorbance (E1) was subtracted from the absorbance (E2) to determine the reaction absorbance ($E_{1C}$) for the sample 1.

Subsequently, the same measurement as above was performed using saline instead of the sample 1 to determine blank absorbance ($E_{blank}$). The blank absorbance ($E_{blank}$) was subtracted from the reaction absorbance ($E_{1C}$) for the sample 1 to determine absorbance ($\Delta E_{1C}$) for the sample 1.

This sequence of operations performed for the sample 1 was also performed for each of the samples 2 to 4 to determine absorbance ($\Delta E_{2C}$) for the sample 2, absorbance ($\Delta E_{3C}$) for the sample 3, and absorbance ($\Delta E_{4C}$) for the sample 4. The relative values of the absorbances ($\Delta E_{2C}$ to $\Delta E_{4C}$) for the samples 2 to 4 to the absorbance ($\Delta E_{1C}$) for the sample 1 as 100 are shown in Table 8.

In addition, relative values of respective absorbances ($\Delta E_{1c}$ to $\Delta E_{4c}$) for the samples 1 to 4 were determined in the same way as above except that the kit c prepared in the paragraph (2) was used instead of the kit C prepared in the paragraph (1). The relative values of the absorbances ($\Delta E_{2c}$ to $\Delta E_{4c}$) for the samples 2 to 4 to the absorbance ($\Delta E_{1c}$) for the sample 1 as 100 are shown in Table 8.

TABLE 8

| Sample | | Relative value of absorbance | |
| --- | --- | --- | --- |
| Sample No. | Dispanol TOC (%) | Kit c | Kit C |
| Sample 1 | 0 | 100 | 100 |
| Sample 2 | 0.05 | 175 | 93 |
| Sample 3 | 0.1 | 251 | 95 |
| Sample 4 | 0.2 | 379 | 100 |

As is evident from Table 8, in the fructosyl VHLTPE quantification system using the leuco chromogen DA-67, the measurement using the kit C comprising pyruvic acid significantly suppressed the influence of Dispanol TOC-derived peroxides, compared with the measurement using the kit c comprising no pyruvic acid, demonstrating that the measurement using the kit C gives a more accurate measurement of fructosyl VHLTPE.

Example 4

Study of Effect of Reducing Influence of Peroxides in Reagent on Glucose Measuring System by α-Keto Acid (1) Kit for Measurement of Glucose Comprising Pyruvic Acid Each of the kits for measurement of glucose (kits D1 to D3) having the following compositions was prepared. The kit D1 represents a kit having a Nonion E230 concentration of 0% in the first reagent. The kit D2 represents a kit having a Nonion E230 concentration of 0.02% in the first reagent. The kit D3 represents a kit having a Nonion E230 concentration of 0.1% in the first reagent.

First Reagent

| MES (pH 6.5) | 50 mmol/L |
| --- | --- |
| EMSE | 0.3 g/L |
| Nonion E230 | 0, 0.02, or 0.1% |
| Sodium pyruvate | 5 g/L |

Second Reagent

| MES (pH 6.5) | 50 mmol/L |
| --- | --- |
| 4-AA | 0.1 g/L |
| POD | 40 kU/L |
| GOD | 100 kU/L |

(2) Kit for Measurement of Glucose Comprising α-Ketoglutaric Acid

Each of the kits for measurement of glucose (kits E1 to E3) having the following compositions was prepared. The kit E1 represents a kit having a Nonion E230 concentration of 0% in the first reagent. The kit E2 represents a kit having a Nonion E230 concentration of 0.02% in the first reagent. The kit E3 represents a kit having a Nonion E230 concentration of 0.1% in the first reagent.

First Reagent

| MES (pH 6.5) | 50 mmol/L |
| --- | --- |
| EMSE | 0.3 g/L |
| Nonion E230 | 0, 0.02, or 0.1% |
| α-ketoglutaric acid | 1 g/L |

Second Reagent

| MES (pH 6.5) | 50 mmol/L |
| --- | --- |
| 4-AA | 0.1 g/L |
| POD | 40 kU/L |
| GOD | 100 kU/L |

(3) Kit for Measurement of Glucose Comprising Oxaloacetic Acid

Each of the kits for measurement of glucose (kits F1 to F3) having the following compositions was prepared. The kit F1 represents a kit having a Nonion E230 concentration of 0% in the first reagent. The kit F2 represents a kit having a Nonion E230 concentration of 0.02% in the first reagent. The kit F3 represents a kit having a Nonion E230 concentration of 0.1% in the first reagent.

First Reagent

| MES (pH 6.5) | 50 mmol/L |
| --- | --- |
| EMSE | 0.3 g/L |
| Nonion E230 | 0, 0.02, or 0.1% |
| Oxaloacetic acid | 0.2 g/L |

Second Reagent

| MES (pH 6.5) | 50 mmol/L |
| --- | --- |
| 4-AA | 0.1 g/L |
| POD | 40 kU/L |
| GOD | 100 kU/L |

(4) Kit for Measurement of Glucose Comprising No α-Keto Acid

Each of the kits for measurement of glucose (kits d1 to d3) having the following compositions was prepared. The kit d1 represents a kit having a Nonion E230 concentration of 0% in the first reagent. The kit d2 represents a kit having a Nonion E230 concentration of 0.02% in the first reagent. The kit d3 represents a kit having a Nonion E230 concentration of 0.1% in the first reagent.

First Reagent

| MES (pH 6.5) | 50 mmol/L |
| --- | --- |
| EMSE | 0.3 g/L |
| Nonion E230 | 0, 0.02, or 0.1% |

Second Reagent

| MES (pH 6.5) | 50 mmol/L |
| --- | --- |
| 4-AA | 0.1 g/L |
| POD | 40 kU/L |
| GOD | 100 kU/L |

(5) Evaluation of Effect of Suppressing Influence of Peroxides by Pyruvic Acid

Saline (2.0 μL) was reacted at 37° C. for 5 minutes with the first reagent (180 μL) of the kit D1 prepared in the paragraph (1). The absorbance (E1) was measured at a main wavelength of 546 nm and a sub-wavelength of 700 nm. Subsequently, the second reagent (60 μL) of the kit D1 was added thereto and further reaction was continued at 37° C. for 5 minutes. The absorbance (E2) was measured at a main wavelength of 546 nm and a sub-wavelength of 700 nm. The measurement was performed using Hitachi H7170. The absorbance (E1) was subtracted from the absorbance (E2) to determine the blank absorbance ($E_{D1}$) for saline.

Subsequently, the same measurement as above was performed using the kit D2 instead of the kit D1 to calculate the blank absorbance ($E_{D2}$) for saline.

In addition, the same measurement as above was performed using the kit D3 instead of the kit D1 to calculate the blank absorbance ($E_{D3}$) for saline.

The blank absorbance ($\Delta E_{D1}$) for the kit D1 was defined as 0, and the blank absorbance ($E_{D1}$) was subtracted from the blank absorbance ($E_{D2}$) to determine the blank absorbance ($\Delta E_{D2}$) for the kit D2. Similarly, the blank absorbance ($E_{D1}$) was subtracted from the blank absorbance ($E_{D3}$) to determine the blank absorbance ($\Delta E_{D3}$) for the kit D3. The respective blank absorbances ($\Delta E_{D1}$ to $\Delta E_{D3}$) for the kits D1 to D3 are shown in Table 9.

(6) Evaluation of Effect of Suppressing Influence of Peroxides by α-Ketoglutaric Acid The respective blank absorbances ($\Delta E_{E1}$ to $\Delta E_{E3}$) for the kits E1 to E3 were calculated in the same way as in the paragraph (5) except that the kits E1 to E3 comprising α-ketoglutaric acid, prepared in the paragraph (2), were used instead of the kits D1 to D3, respectively. The respective blank absorbances ($\Delta E_{E1}$ to $\Delta E_{E3}$) for the kits E1 to E3 are shown in Table 9.

(7) Evaluation of Effect of Suppressing Influence of Peroxides by Oxaloacetic Acid The respective blank absorbances ($\Delta E_{F1}$ to $\Delta E_{F3}$) for the kits F1 to F3 were calculated in the same way as in the paragraph (5) except that the kits F1 to F3 comprising oxaloacetic acid, prepared in the paragraph (3), were used instead of the kits D1 to D3, respectively. The respective blank absorbances ($\Delta E_{F1}$ to $\Delta E_{F3}$) for the kits F1 to F3 are shown in Table 9.

(8) Evaluation of Effect of Suppressing Influence of Peroxides Using Kit Comprising No α-Keto Acid The respective blank absorbances ($\Delta E_{d1}$ to $\Delta E_{d3}$) for the kits d1 to d3 were calculated in the same way as in the paragraph (5) except that the kits d1 to d3 comprising no α-keto acid, prepared in the paragraph (4), were used instead of the kits D1 to D3, respectively. The respective blank absorbances ($\Delta E_{d1}$ to $\Delta E_{d3}$) for the kits d1 to d3 are shown in Table 9.

TABLE 9

| Nonion E230 | Blank absorbance (mAbs) | | | | | | | |
|---|---|---|---|---|---|---|---|---|
| | No α-keto acid | | Pyruvic acid | | α-ketoglutaric acid | | Oxaloacetic acid | |
| 0% | 0.0 | $\Delta E_{d1}$ | 0.0 | $\Delta E_{D1}$ | 0.0 | $\Delta E_{E1}$ | 0.0 | $\Delta E_{F1}$ |
| 0.02% | 4.6 | $\Delta E_{d2}$ | 0.0 | $\Delta E_{D2}$ | 0.6 | $\Delta E_{E2}$ | 0.4 | $\Delta E_{F2}$ |
| 0.1% | 17.2 | $\Delta E_{d3}$ | 2.2 | $\Delta E_{D3}$ | 5.0 | $\Delta E_{E3}$ | 5.6 | $\Delta E_{F3}$ |

As is evident from Table 9, it proved that in case of using the kits comprising pyruvic acid, α-ketoglutaric acid, or oxaloacetic acid as α-keto acid, blank absorbance was significantly reduced, even at high Nonion E230 concentrations, compared with in case of using the kits comprising no α-keto acid. The Nonion E230 is a surfactant that tends to form peroxides. These results demonstrated that α-keto acid significantly suppresses the influence of peroxides originated from Nonion E230 to give a more accurate measurement of glucose.

Example 5

Study of Effect of Suppressing Influence of Peroxides in Reagent on Hemoglobin A1c Measuring System by α-Keto Acid (1) Kit for Measurement of Hemoglobin A1c Comprising Pyruvic Acid A kit for measurement of hemoglobin A1c (kit G) having the following composition was prepared:
First Reagent

| MES (pH 6.5) | 50 mmol/L |
| Calcium chloride dihydrate | 10 mmol/L |
| Sodium nitrate | 100 mmol/L |
| 1-dodecylpyridinium chloride | 1.4 g/L |
| Actinase E | 340 kU/L |
| DA-67 | 30 μmol/L |
| Nonion E230 | 0.01% |
| Sodium pyruvate | 2 g/L |

Second Reagent

| Bis-Tris (pH 7.0) | 50 mmol/L |
| FPOX-CET | 6 kU/L |
| POD | 120 kU/L |

(2) Kit for Measurement of Hemoglobin A1c Comprising α-Ketoglutaric Acid

A kit for measurement of hemoglobin A1c (kit H) having the following composition was prepared:
First Reagent

| MES (pH 6.5) | 50 mmol/L |
| Calcium chloride dihydrate | 10 mmol/L |
| Sodium nitrate | 100 mmol/L |
| 1-dodecylpyridinium chloride | 1.4 g/L |
| Actinase E | 340 kU/L |
| DA-67 | 30 μmol/L |
| Nonion E230 | 0.01% |
| α-ketoglutaric acid | 0.3 g/L |

Second Reagent

| Bis-Tris (pH 7.0) | 50 mmol/L |
| FPOX-CET | 6 kU/L |
| POD | 120 kU/L |

(3) Kit for Measurement of Hemoglobin A1c Comprising Oxaloacetic Acid

A kit for measurement of hemoglobin A1c (kit I) having the following composition was prepared:
First Reagent

| MES (pH 6.5) | 50 mmol/L |
| Calcium chloride dihydrate | 10 mmol/L |

-continued

| Sodium nitrate | 100 mmol/L |
|---|---|
| 1-dodecylpyridinium chloride | 1.4 g/L |
| Actinase E | 340 kU/L |
| DA-67 | 30 μmol/L |
| Nonion E230 | 0.01% |
| Oxaloacetic acid | 0.3 g/L |

Second Reagent

| Bis-Tris (pH 7.0) | 50 mmol/L |
|---|---|
| FPOX-CET | 6 kU/L |
| POD | 120 kU/L |

(4) Kit for Measurement of Hemoglobin A1c Comprising No α-Keto Acid

A kit for measurement of hemoglobin A1c (kit e) having the following composition was prepared:

First Reagent

| MES (pH 6.5) | 50 mmol/L |
|---|---|
| Calcium chloride dihydrate | 10 mmol/L |
| Sodium nitrate | 100 mmol/L |
| 1-dodecylpyridinium chloride | 1.4 g/L |
| Actinase E | 340 kU/L |
| DA-67 | 30 μmol/L |
| Nonion E230 | 0.01% |

Second Reagent

| Bis-Tris (pH 7.0) | 50 mmol/L |
|---|---|
| FPOX-CET | 6 kU/L |
| POD | 120 kU/L |

(5) Evaluation of Effect of Suppressing Influence of Peroxides by Pyruvic Acid

Each of blood cells having a hemoglobin A1c concentration of 3.2, 4.0, 4.9, 5.6, 6.5, 7.6, and 9.7 μmol/L, respectively, and saline (hemoglobin A1c concentration: 0 μmol/L) were used as samples.

Each sample (12 μL) was reacted at 37° C. for 5 minutes with the first reagent (150 μL) of the kit G comprising pyruvic acid, prepared in the paragraph (1). The absorbance (E1) was measured at a main wavelength of 660 nm and a sub-wavelength of 800 nm. Subsequently, the second reagent (50 μL) of the kit G was added thereto and further reaction was continued at 37° C. for 5 minutes. The absorbance (E2) was measured at a main wavelength of 660 nm and a sub-wavelength of 800 nm. The measurement was performed using Hitachi H7170. The absorbance (E1) was subtracted from the absorbance (E2) to determine the reaction absorbance ($E_G$) for each sample in the kit G.

Figure 1:
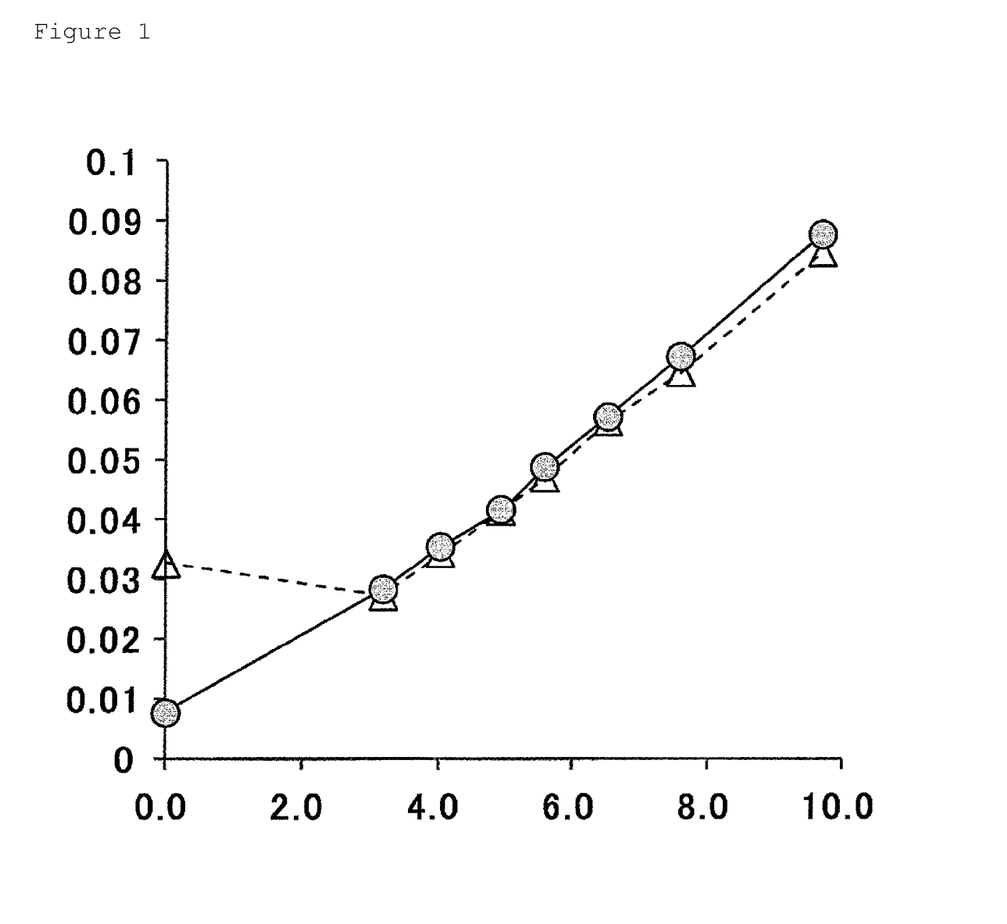
FIG. 1 is a graph showing the relationship between hemoglobin A1c concentration and absorbance in a method for measuring hemoglobin A1c using a kit for hemoglobin A1c measurement comprising pyruvic acid in Example 5(1) or a kit for hemoglobin A1c measurement comprising no α-keto acid in Example 5(4). The abscissa represents hemoglobin A1c concentration (μmol/L), and the ordinate represents absorbance (Abs). ○ represents the graph of measurement using the kit comprising pyruvic acid. Δ represents the graph of measurement using the kit comprising no α-keto acid.

The reaction absorbance ($E_e$) for each sample in the kit e was calculated in the same way as above using the kit e of (4) comprising no α-keto acid and used as a control. FIG. 1 shows the reaction absorbance ($E_G$) for each sample in the kit G and the reaction absorbance ($E_e$) for each sample in the kit e.

Figure 2:
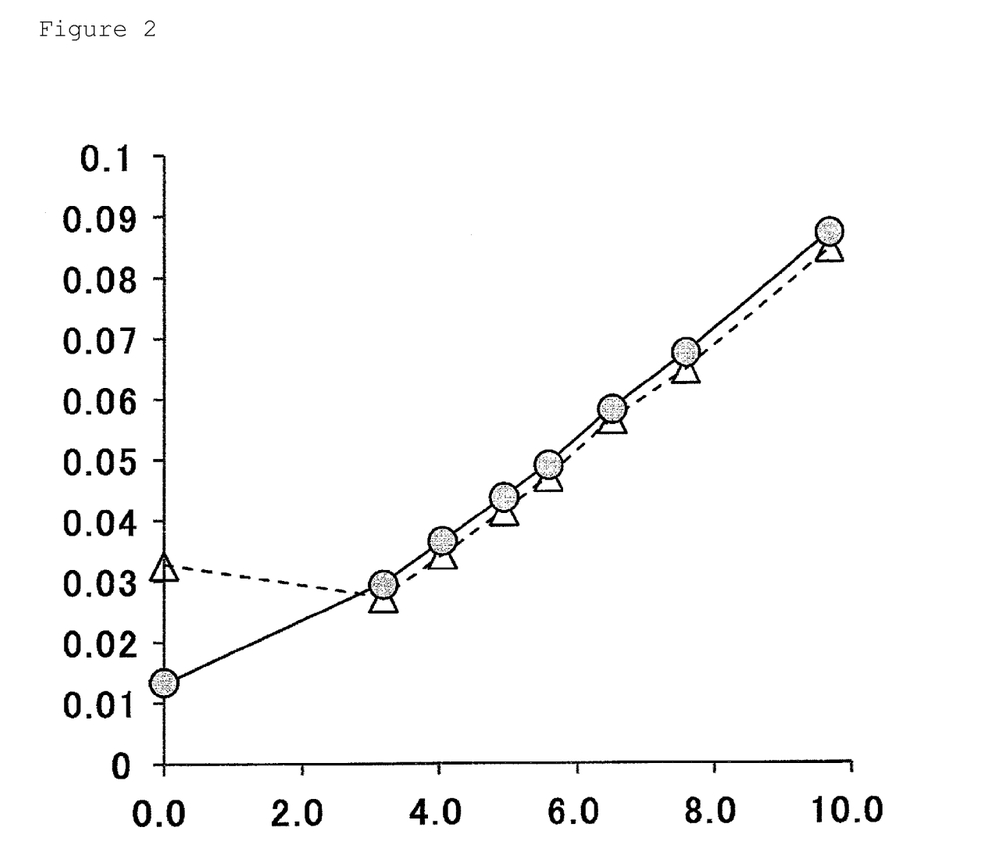
FIG. 2 is a graph showing the relationship between hemoglobin A1c concentration and absorbance in a method for measuring hemoglobin A1c using a kit for hemoglobin A1c measurement comprising α-ketoglutaric acid in Example 5(2) or a kit for hemoglobin A1c measurement comprising no α-keto acid in Example 5(4). The abscissa represents hemoglobin A1c concentration (μmol/L), and the ordinate represents absorbance (Abs). ○ represents the graph of measurement using the kit comprising α-ketoglutaric acid. Δ represents the graph of measurement using the kit comprising no α-keto acid.

(6) Evaluation of Effect of Suppressing Influence of Peroxides by α-Ketoglutaric Acid The reaction absorbance ($\Delta E_H$) for each sample in the kit H was calculated in the same way as in the paragraph (5) except that the kit H comprising α-ketoglutaric acid, prepared in the paragraph (2), was used instead of the kit G. FIG. 2 shows the reaction absorbance ($E_H$) for each sample in the kit H and the reaction absorbance ($E_e$) for each sample in the kit e.

Figure 3:
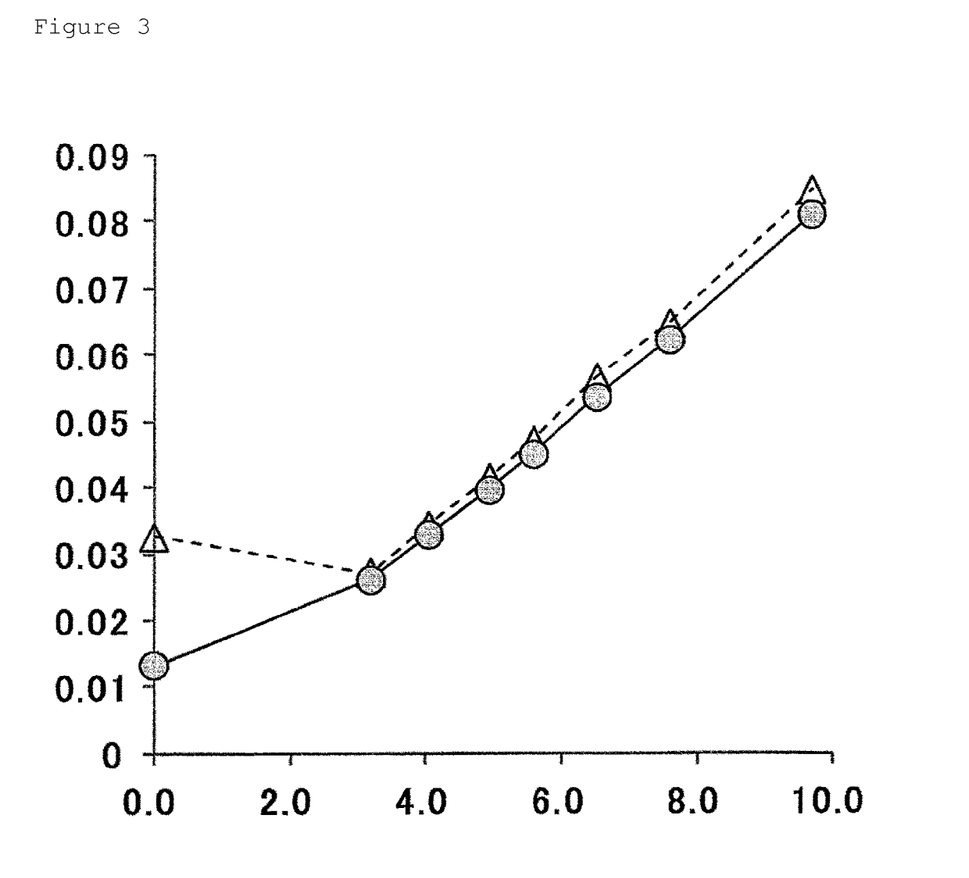
FIG. 3 is a graph showing the relationship between hemoglobin A1c concentration and absorbance in a method for measuring hemoglobin A1c using a kit for hemoglobin A1c measurement comprising oxaloacetic acid in Example 5(3) or a kit for hemoglobin A1c measurement comprising no α-keto acid in Example 5(4). The abscissa represents hemoglobin A1c concentration (μmol/L), and the ordinate represents absorbance (Abs). ○ represents the graph of measurement using the kit comprising oxaloacetic acid. Δ represents the graph of measurement using the kit comprising no α-keto acid.

(7) Evaluation of Effect of Suppressing Influence of Peroxides by Oxaloacetic Acid The reaction absorbance ($\Delta E_I$) for each sample in the kit I was calculated in the same way as in the paragraph (5) except that the kit I comprising oxaloacetic acid, prepared in the paragraph (3), was used instead of the kit G. FIG. 3 shows the reaction absorbance ($E_I$) for each sample in the kit I and the reaction absorbance ($E_e$) for each sample in the kit e.

As is evident from FIGS. 1 to 3, absorbance originated from a peroxide-derived coloring was obtained as a blank in the measurement using the kit comprising no α-keto acid in the case of using saline as the sample. Also, absorbance lower than the blank absorbance was obtained in the case of using the blood cell having a hemoglobin A1c concentration of 3.2 μmol/L as the sample. This is probably due to elimination of peroxides and hemoglobin A1c-derived hydrogen peroxide by the reduction effect of hemoglobin contained in the blood cell.

By contrast, in the measurement using the kits comprising each α-keto acid, no decrease in absorbance was observed even in the case of using the blood cell having a hemoglobin A1c concentration of 3.2 μmol/L. Favorable linearity was confirmed between the hemoglobin A1c concentration and the absorbance. This is probably because the α-keto acid interacts with peroxides to eliminate the peroxides, whereas the α-keto acid neither interacts with hydrogen peroxide nor eliminates hemoglobin A1c-derived hydrogen peroxide.

Thus, it proved that the kit comprising pyruvic acid, α-ketoglutaric acid, or oxaloacetic acid suppressed the influence of Nonion E230-derived peroxides on the measurement to give a more accurate measurement of hemoglobin A1c concentration.

INDUSTRIAL APPLICABILITY

The present invention provides a method for measuring a component to be measured in a sample, a reagent therefore, and a kit therefore, whereby the influence of a peroxide on the hydrogen peroxide quantification system is suppressed, and also provides a method for suppressing the influence of a peroxide. The present invention is useful in clinical diagnosis, and the like.

The invention claimed is:

1. A method for suppressing the influence of a peroxide on a method for measuring hemoglobin A1c in a sample containing peroxides comprising the steps of:
    adding an α-keto acid to an aqueous solution containing the sample to react with the peroxides contained therein;
    converting hemoglobin A1c into hydrogen peroxide in the aqueous solution; and
    reacting the formed hydrogen peroxide with an oxidative-coloring chromogen in the presence of the α-keto acid, whereby
    influence of the peroxides other than said formed hydrogen peroxide on said reaction of said hydrogen peroxide with said oxidative-coloring chromogen is suppressed.

2. The method according to claim 1, wherein the α-keto acid is an α-keto acid selected from the group consisting of pyruvic acid, α-ketoglutaric acid, and oxaloacetic acid.

3. The method according to claim 1, wherein the oxidative-coloring chromogen is a leuco chromogen.

4. The method according to claim 3, wherein the leuco chromogen is a phenothiazine derivative.

5. The method according to claim 4, wherein the phenothiazine derivative is 10-(carboxymethylaminocarbonyl)-3,7-bis(dimethylamino)phenothiazine.

6. The method according to claim 1, wherein the oxidative-coloring chromogen is an oxidative coupling-type chromogen.

7. The method according to claim 6, wherein the oxidation coupling-type chromogen is a combination of a coupler and an aniline derivative or a phenol derivative.

* * * * *

UNITED STATES PATENT AND TRADEMARK OFFICE
CERTIFICATE OF CORRECTION

PATENT NO. : 9,671,348 B2
APPLICATION NO. : 13/991652
DATED : June 6, 2017
INVENTOR(S) : Tomomi Murakami It is certified that error appears in the above-identified patent and that said Letters Patent is hereby corrected as shown below:

On the Title Page

[56] REFERENCES CITED:
Other Publications, Insert:
--Oguri et al., "screening of D-amino acid oxidase inhibitor by a new multi-assay method", Food Chemistry, Vol. 100, No. 2 (2007) 616-22--.

In the Specification

Column 8:
Line 30, "reagent" should read --reagent from among--.

Column 24:
Line 41, "therefore," should read --therefor,--; and
Line 42, "therefore," should read --therefor,--.

Signed and Sealed this
Fifth Day of December, 2017

Joseph Matal
*Performing the Functions and Duties of the
Under Secretary of Commerce for Intellectual Property and
Director of the United States Patent and Trademark Office*